Oct. 15, 1968 A. C. CURCIO ET AL Plant Pat. 2,839
NECTARINE TREE
Filed Feb. 2, 1967
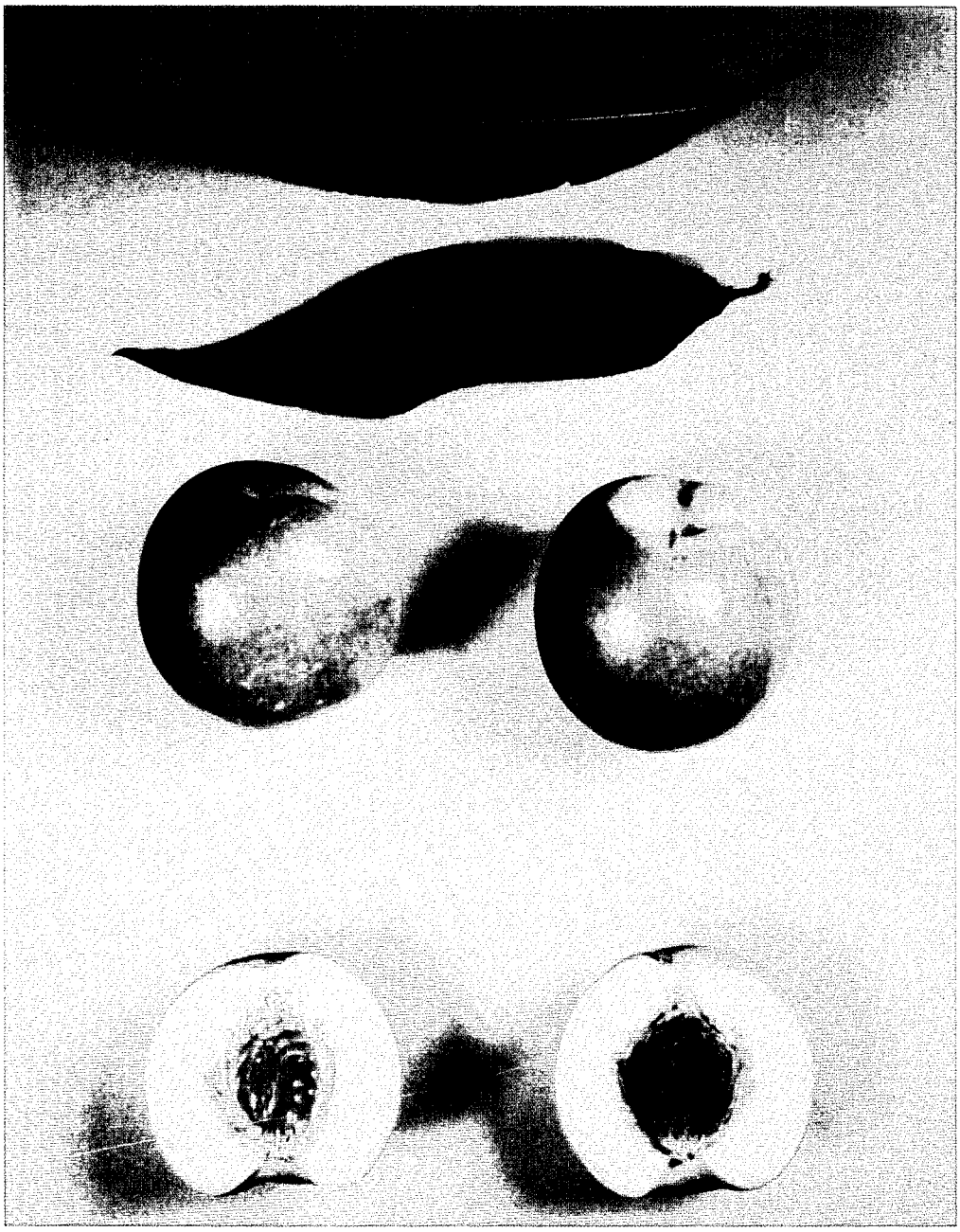
Inventors.
A. C. Curcio
N. C. Curcio
By: Robb & Robb
Attorneys.

United States Patent Office

Plant Pat. 2,839
Patented Oct. 15, 1968

2,839
NECTARINE TREE

Anthony C. Curcio and Nunzio C. Curcio, Hammonton, N.J., assignors to Edgar H. Kemp and Homer S. Kemp, co-partners, trading as Bountiful Ridge Nurseries, Princess Anne, Md.

Filed Feb. 2, 1967, Ser. No. 613,689
1 Claim. (Cl. Plt.—41)

The present invention relates to a new and distinct variety of nectarine tree which was discovered by us as a newly found seedling of unknown parentage, on our cultivated fruit farm property located at 1005 N. Egg Harbor Road, Hammonton, N.J.

At the time of our discovery aforementioned, our attention was attracted to the new seedling, which was found growing very close to the packing house on our fruit farm, by reason of the large size and exceptional attractive appearance of its fruit which was definitely different from the fruit of any other variety then being grown by us. Closer study of the fruit indicated that it also was of superior quality and flavor, and convinced us that it was a new, distinct and improved variety which would successfully compete commercially with the best previously known varieties which usually have been grown in the past in the Western States, and that the fruit of our new variety would bring high prices on our large commercial markets and give impetus to larger plantings all over the Eastern States wherever peaches can be grown, for both commercial markets and home use.

Since we were preparing to build an addition to our packing shed, the original tree had to be removed, and buds were take therefrom and budded to a "Sunhaven" peach tree (unpatented), and subsequent buddings have also been made elsewhere for test purposes on our behalf. Observations of the progeny so derived have satisfied us, as well as other growers and experts who have observed our new variety, that it is definitely distinguished from all other varieties, as evidenced by the following unique combination of characteristics which are outstanding therein:

(1) A thrifty and productive tree habit;
(2) A large fruit size;
(3) An attractive high coloring of the fruit skin when mature, with bright Red being the dominant color and merging with bright Yellow on the remainder of the skin;
(4) An excellent fruit flavor; and
(5) Good fruit keeping qualities and resistance to bruises.

The accompanying drawing shows typical specimens of the foliage and fruit of our new variety as depicted in color as nearly true as it is reasonably possible to make the same in a color illustration of this character, said fruit being shown in elevation and also in cross-section, with one half-section exposing the cavity and the other half-section exposing the stone seated in the cavity, and the foliage specimens depicting both the upper and under surfaces of typical leaves.

The following is a detailed description of the new variety, with color terminology in accordance with Maerz and Paul Dictionary of Color, except where general color terms of ordinary dictionary signficance are obvious:

Locality where grown and observed: Hammonton, N.J.
Dates of first and last pickings: August 20 and September 10, respectively.

Tree: Medium large; vigorous; upright; dense; round topped; hardy; productive; regular bearer.
*Trunk.*—Medium smooth.
*Branches.*—Stocky; smooth. Color—Miradon Red, Plate 8, L–6 at first, becoming Green, Plate 15, L–8. Lenticels—numerous; large.
*Leaves.*—Medium thickness; rugose. Size—medium; length—from 5½ inches to 7 inches; width—from 1⅜ inches to 1⅝ inches. Shape—lanceolate; acutely pointed. Color:—upper side—Green, Plate 24, L–2; under side—Green, Plate 23, J–6. Margin — crenate; finely serrate. Petiole — medium length; thick. Glands—usually 3; alternate; medium; mixed; positioned at base and petiole of leaf blade; color—Green. Stipules—none.
Flower buds: Hardy; large size; medium length; obtuse; appressed; pubescent.
Flowers:
*Dates of first and full bloom.*—About April 12 and April 21, respectively; medium earliness.
*Size.*—Medium large.
*Color.*—Peach Blossom, Plate 1, C–2.
Fruit:
*Maturity when described.*—Eating ripe. Date—September 1.
*Size.*—Large; uniform. Axial diameter—about 2¾ inches. Transverse diameter in suture plane—about 2¾ inches. Diameter at right angles to suture plane—about 2¾ inches.
*Form.*—Uniform; symmetrical; globose; oblate; compressed transversely.
*Suture.*—Distinct; extends from base to apex over entire circumference; has slight depression beyond pistil point.
*Ventral surface.*—Rounded slightly; lipped toward base on both sides; lips equal.
*Cavity.*—Flaring; elongated in suture plane with suture plane with suture show-on both sides. Depth—½ inch. Breadth—from 1 inch to 1¼ inches. Markings—Red coloring of skin blends into Yellow skin color.
*Base.*—Rounded.
*Apex.*—Short; from rounded to truncate; slightly depressed pistil point.
*Stem.*—Stout; pubescent; glabrous; strong adherence to stone. Length—⅜ inch.
*Skin.*—Thick; tough; tenacious to flesh; no tendency to crack during wet or dry seasons. Color—Red, Plate 4, L–10, merging into Holly Berry Yellow, Plate 9, K–5. Down—wanting.
*Flesh.*—Color—Yellow, Plate 9, L–6 mottled with Red, Plate 3, L–6 next to stone throughout.
*Surface of pit cavity.* — Color — Red, with Yellow fibres.
*Amygdalin.*—wanting.
*Juice.*—Moderate abundance; rich.
*Texture.*—Firm; crisp; meaty; melting.
*Fibres.*—Few; coarse; tender.
*Ripens.*—Evenly.
*Flavor.*—Subacid; mild; delicate.
*Aroma.*—Pronounced; distinct.
*Eating quality.*—Best.
Stone: Free; long fibres; parts from flesh smoothly.
*Size.*—Medium. Length—1¼ inches. Breadth—1 inch. Thickness—from ⅝ inch to ¾ inch.

*Form.*—Obovoid.
*Base.*—Oblique.
*Hilum.*—From oval to oblong.
*Apex*—Acuminate.
*Sides.*—Unequal; curved on right and left sides.
*Surface.*—Irregularly furrowed near base and toward apex throughout; pitted throughout.
*Ridges.*—Rounded.
*Pits.*—Elongated.
*Ventral edge.*—Thick; with wing toward base.
*Dorsal edge.*—Narrow, with shallow groove throughout; ridges interrupted.

Insect and disease resistance: Good resistance to common insects and diseases to which nectarines are normally subject, as determined by comparison with other varieties grown under the same cultural conditions at Hammonton, N.J.

Use: Market; local; dessert; culinary; commercial canning.
Keeping quality: Good.
Shipping quality: Good.

We claim:

1. A new and distinct variety of nectarine tree of the Yellow fleshed freestone fruit bearing class, substantially as therein shown and described, characterized as to novelty by the unique combination of a thrifty and productive tree habit, a large fruit size, an attractive high coloring of the fruit skin when mature, with bright Red being the dominant color and merging with bright Yellow on the remainder of the skin, an excellent fruit flavor, and good fruit keeping qualities and resistance to bruises.

No references cited.

ROBERT E. BAGWILL, *Primary Examiner.*